United States Patent [19]

Marumo et al.

[11] 4,178,462
[45] Dec. 11, 1979

[54] NOVEL BICYCLODECADIENE COMPOUNDS AND PROCESS FOR PRODUCING THEM

[75] Inventors: Shingo Marumo, Owariasahi; Masato Katayama, Nagoya, both of Japan

[73] Assignee: Noda Institute For Scientific Research, Noda, Japan

[21] Appl. No.: 945,831

[22] Filed: Sep. 26, 1978

[30] Foreign Application Priority Data

Sep. 29, 1977 [JP] Japan .................................. 52-116139
Mar. 9, 1978 [JP] Japan .................................. 53-25942

[51] Int. Cl.² ........................................... C07C 61/28
[52] U.S. Cl. ................................... 562/501; 260/598; 424/317; 424/333; 435/136; 435/147
[58] Field of Search ......................................... 562/501

[56] References Cited

PUBLICATIONS

Chemical Abstracts 37, 115/4.

*Primary Examiner*—Robert Gerstl

[57] ABSTRACT

5-Isopropyl-8-methyl bicyclo[5.3.0]deca-2,8-diene-2-carboxylic acid having a chemical structure represented by the following formula:

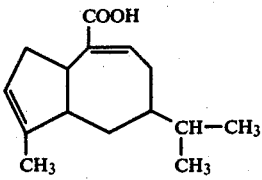

and 5-isopropyl-8-methyl bicyclo[5.3.0]deca-2,8-diene-2-carboaldehyde having a chemical structure represented by the following formula:

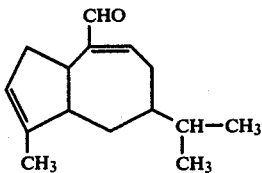

can be obtained by cultivating a microbial strain belonging to Genus Sclerotinia and having an ability to produce them, and collecting them from the cultivated mixture.

2 Claims, 8 Drawing Figures

NOVEL BICYCLODECADIENE COMPOUNDS AND PROCESS FOR PRODUCING THEM

This invention relates to 5-isopropyl-8-methyl bicyclo[5.3.0]deca-2,8-diene-2-carboxylic acid (hereinafter abbreviated to SF-1 substance) and 5-isopropyl-8-methyl bicyclo[5.3.0]deca-2,8-diene-2-carboaldehyde (hereinafter abbreviated to SF-2 substance) which markedly induce the sporulation of microorganisms, particularly molds, and are called sporogenic substance, as well as to a process for producing them.

Although it is well known that in the life cycle of molds, yeasts and bacteria the sporulation progresses in accordance with the change in environmental conditions, nothing has been revealed so far about the substance inducing the sporulation of these microorganisms.

The present inventors have earnestly studied the mechanism of sporulation in molds to find out that two novel bicyclo-decadiene compounds obtainable by extraction of the cultivated mixture of Sclerotinia S-1, separated from plum infected with Monilia disease and rotten, markedly induce the sporulation of molds. Based on this finding, this invention has been accomplished.

Figure 1:
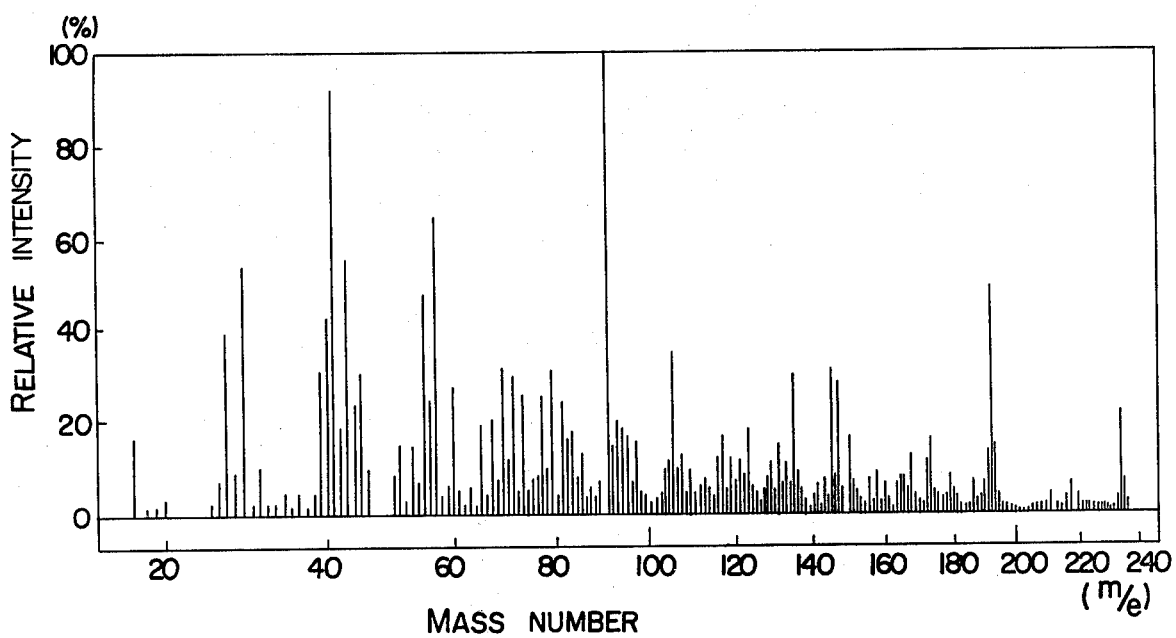
Figure 2:
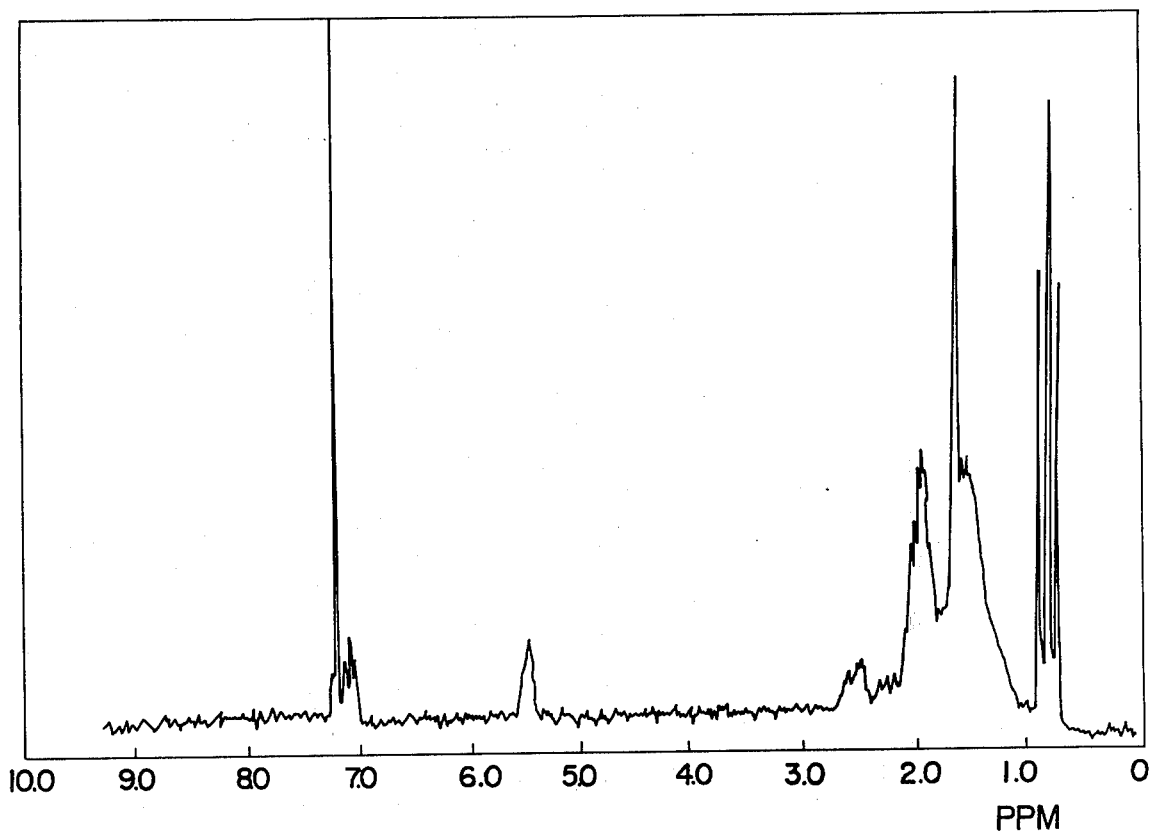
Figure 3:
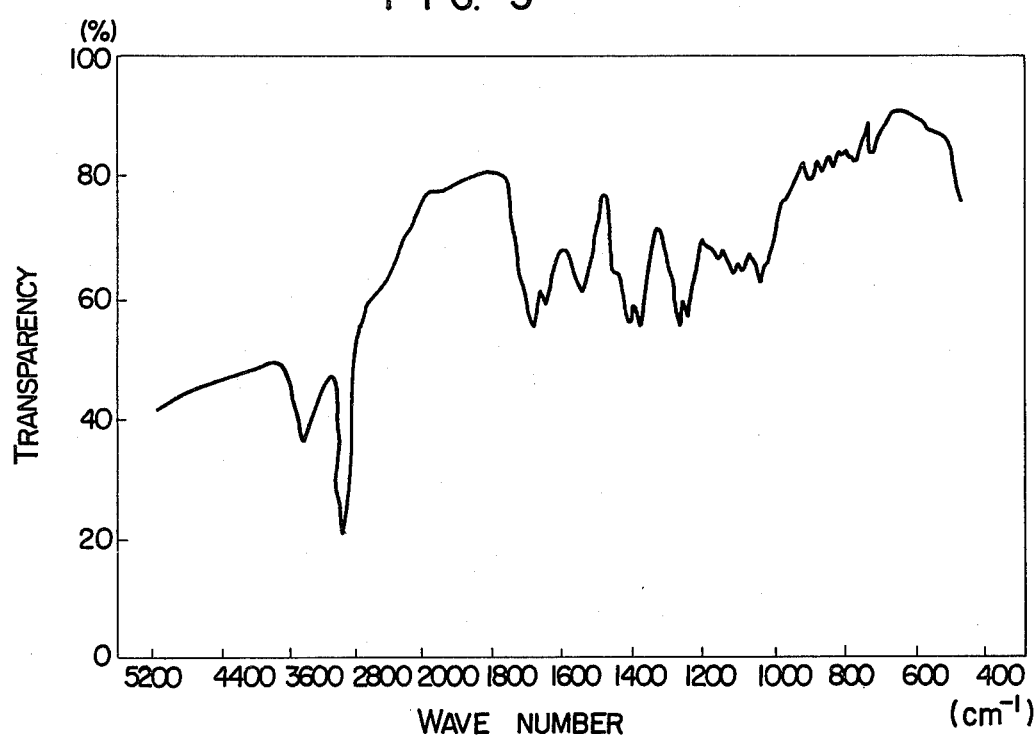
Figure 4:
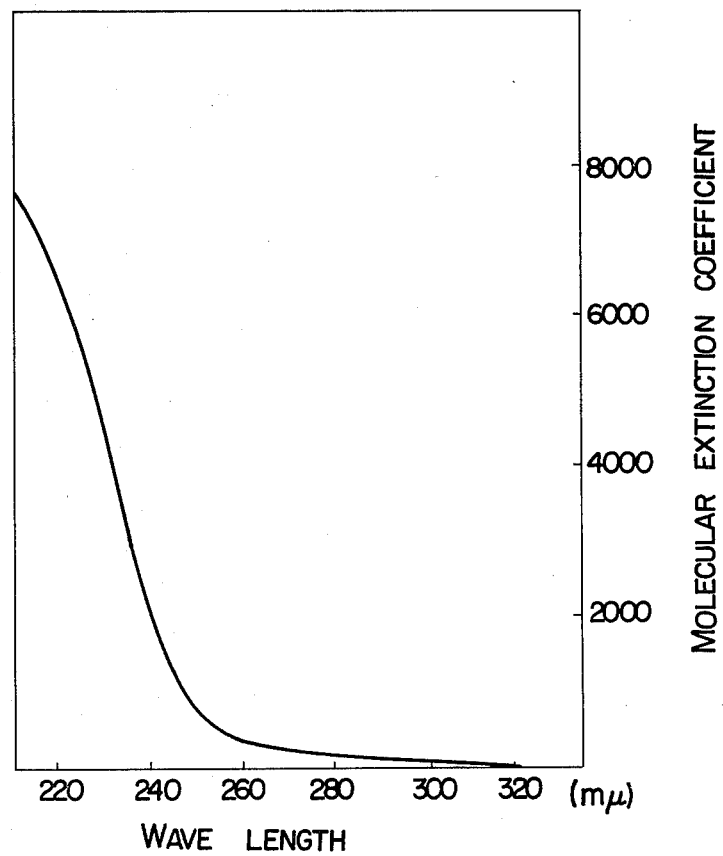
Figure 5:
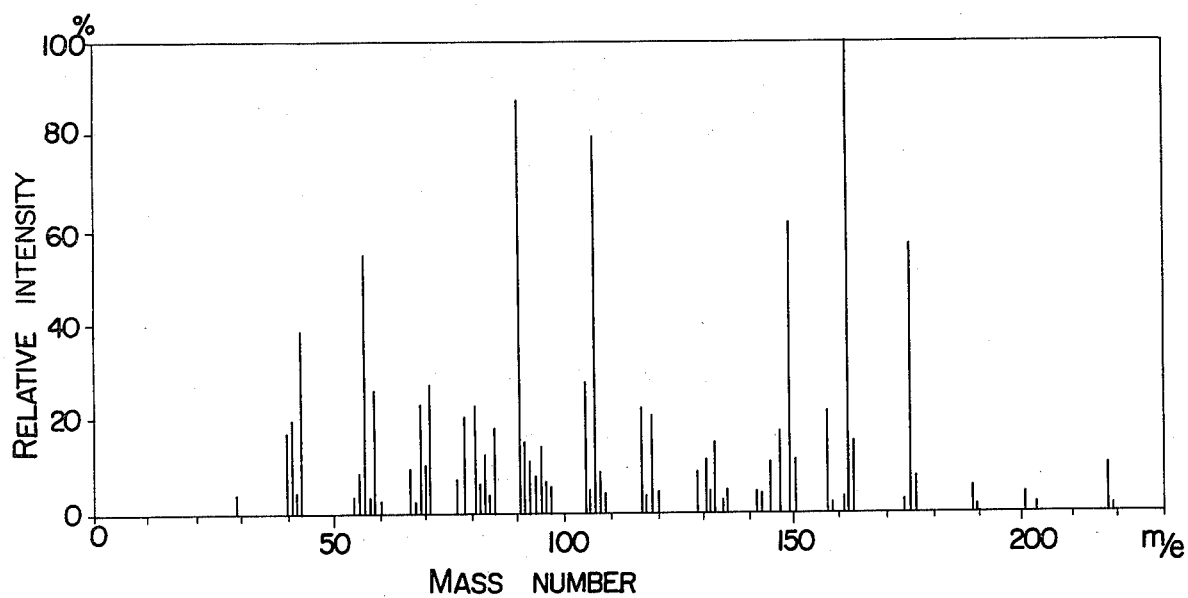
Figure 6:
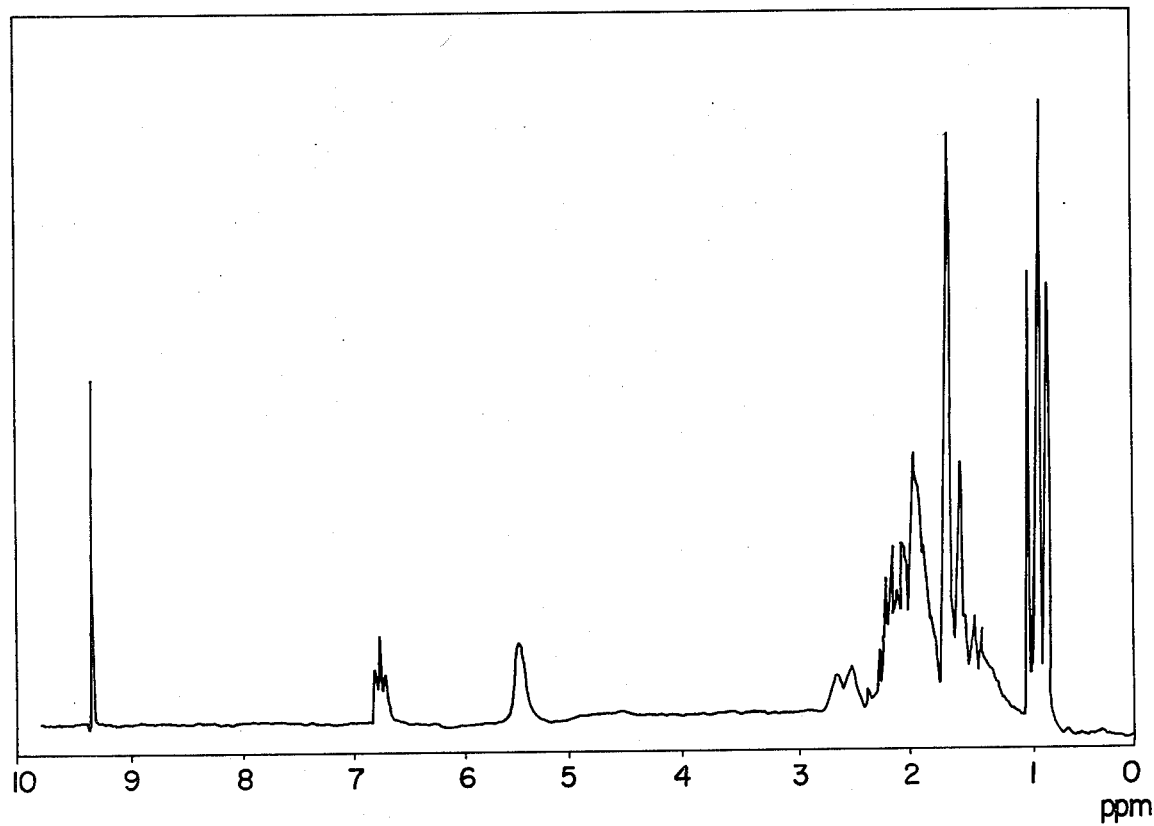
Figure 7:
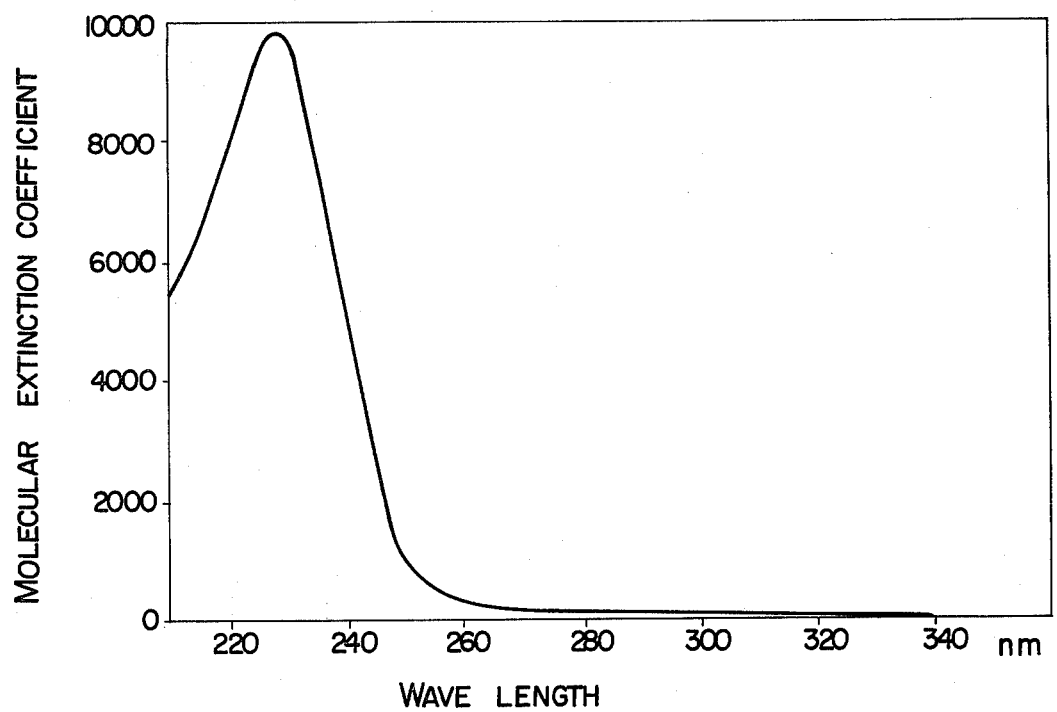
Figure 8:
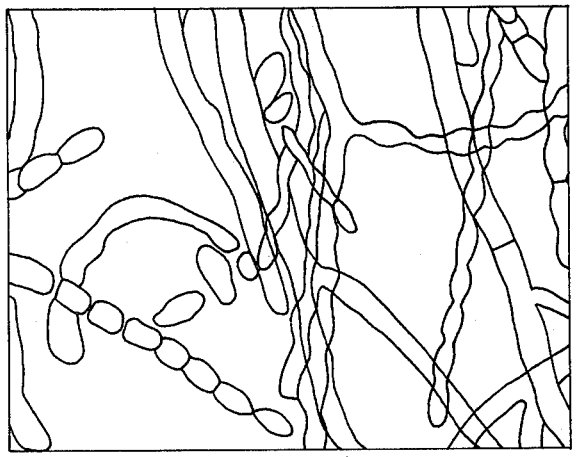

Among the accompanying drawings,

FIG. 1 illustrates the mass spectrum of SF-1 substance,

FIG. 2 illustrates the proton nuclear magnetic resonance spectrum of SF-1 substance, FIG. 3 illustrates the infrared absorption spectrum of SF-1 substance, FIG. 4 illustrates the ultraviolet absorption spectrum of SF-1 substance, FIG. 5 illustrates the mass spectrum of SF-2 substance, FIG. 6 illustrates the proton nuclear magnetic resonance spectrum of SF-2 substance, FIG. 7 illustrates the ultraviolet absorption spectrum of SF-2 substance, and FIG. 8 is a reproduced microscopic view ($\times 400$) of Sclerotinia S-1 (ATCC No. 20497) cultivated in darkness at 25° C. for 7 days in a malt extract agar medium (pH 5.3).

The novel SF-1 substance of this invention, having a sporogenic activity, has the following physicochemical properties:

(1) Color and shape: It forms a colorless plate after recrystallization from dioxane-water system.

(2) Molecular formula: $C_{15}H_{22}O_2$.

(3) Molecular weight: Calculated: 234.1620; Found: 234.1647.

(4) Elementary analysis:

|  | C | H | O |
|---|---|---|---|
| Calculated (%) | 76.88 | 9.46 | 13.65 |
| Found (%) | 76.82 | 9.58 | 13.71 |

(5) Mass spectrum: Shown in FIG. 1. m/e (relative intensity %): 234 (molecular ion $M^+$, 31), 191 (49), 189 (9), 173 (16), 147 (30), 145 (30), 135 (36), 123 (24), 117 (20), 105 (38), 91 (base peak 100), 77 (40), 69 (46), 57 (73), 43 (36), 41 (86).

(6) Proton nuclear magnetic resonance spectrum: FIG. 2 illustrates the spectrum measured in deuterated chloroform at 100 MHz.

δ: 0.84 (3H, d, J=7.1 Hz), 0.92 (3H, d, J=7.1 Hz), 1.69 (3H, s), 1.3–2.4 (10H, m), 2.60 (1H, broad d, J=12.5 Hz), 5.49 (1H, broad s), 7.13 (1H, t, J=3.7 Hz).

(7) Infrared absorption spectrum: FIG. 3 illustrates the spectrum measured by KBr tablet method. $\nu cm^{-1}$: 3425, 2960, 2940, 1690, 1655, 1550, 1460, 1410, 1385, 1270, 1250, 1040.

(8) Ultraviolet absorption spectrum: It shows only an endo absorption as depicted in FIG. 4. $\lambda_{CH_3OH}$: 210 nm (molar extinction coefficient $\epsilon$: 7550).

(9) Circular dichroism: As measured according to "Jikken Kagaku Koza", Vol. 11 (Complex salt chemistry), Pages 317–334 (1956), published by Maruzen K. K., it exhibits a circular-dichroic cotton effect ($[\theta]_{214 nm} = -31.590$), demonstrating a molecular asymmetry.

(10) Solubility: It is soluble in methanol, ethanol, acetone, diethyl ether, ethyl acetate, dioxane and benzene. It is only slightly soluble in water.

(11) $R_f$ value: In silica gel (Kiselgel 60 $PF_{254}$, Merck Corp.) thin layer chromatography (thickness of layer: 0.25 mm, developing solvent: ethyl acetate-n-hexane (3:7), distance of development: 16 cm, temperature of development: room temperature), $R_f = 0.50$.

(12) High performance liquid chromatography: It is eluted at a retention time of 6.0 minutes in silica gel chromatography (silica gel: Lichrosorb RP-2, particle size: 10 μm, Merck Corp.) dimension of column: 4 mm in diameter and 250 mm in length, solvent: dioxane-water (6:4), pressure: 80 kg/cm², flow rate: 1.0 ml/min., detector: UV 234 nm).

SF-1 substance has the following chemical reactivities:

(1) Upon reaction with diazomethane, it gives methyl ester ($C_{16}H_{24}O_2$).

(2) When sprayed with 0.5% vanillin-sulfuric acid on a thin layer of silica gel 60 $PF_{254}$, it assumes red-violet. If heated afterwards, it turns to blue-violet.

(3) When catalytically reduced on palladium black, it absorbs 2 moles of hydrogen to form a tetrahydro compound ($C_{15}H_{26}O_2$).

(4) When reduced medium with lithium aluminum hydride ($LiAlH_4$) in ether, it forms an alcohol ($C_{15}H_{24}O$).

From the physicochemical properties and chemical reactivities mentioned above, it can be deduced that SF-1 substance is 5-isopropyl-8-methyl bicyclo[5.3.0]deca-2,8-diene-2-carboxylic acid represented by the following structural formula:

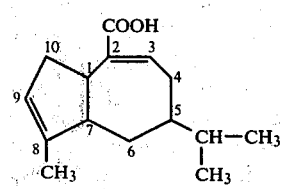

Next, SF-2 substance of this invention has the following physicochemical properties:

(1) Color and shape: Colorless and oily.

(2) Molecular formula: $C_{15}H_{22}O$.

Molecular weight: (calculated from observed values of high-resolution mass spectroscopy). Calculated: 218.1671; Found: 218.1672.

(3) Elementary analysis:

|  | C | H | O |
|---|---|---|---|
| Calculated (%) | 82.52 | 10.16 | 7.33 |
| Found (%) | 82.48 | 10.16 | 7.36 |

(4) Mass spectrum: Shown in FIG. 5. m/e (relative intensity %): 218 (molecular ion M+, 10), 203 (2), 200 (4), 189 (5), 175 (57), 162 (base peak 100), 157 (21), 149 (62), 133 (15), 119 (21), 117 (22), 107 (80), 91 (87), 81 (23), 71 (27), 69 (23), 59 (26), 57 (56), 43 (39), 41 (20), 29 (4).

(5) Proton nuclear magnetic resonance spectrum:

FIG. 6 illustrates the spectrum measured in deuterated chloroform at 100 MHz. δ: 0.84 (3H, d, J=7.1 Hz), 0.93 (3H, d, J=7.1 Hz), 1.69 (3H, s), 1.2–2.4 (9H), 2.60 (1H, d, J=12.4 Hz), 5.52 (1H, broad s, half-value width 8 Hz), 6.80 (1H, t, J=5.1 Hz), 9.40 (1H, s).

(6) Ultraviolet absorption spectrum: FIG. 7 illustrates the spectrum measured in n-hexane. $\lambda_{max}$ 228 nm (molar extinction coefficient ε: 9760).

(7) Circular dichroism: As measured in n-hexane according to "Jikken Kagaku Koza" Vol. 11 (Complex salt chemistry), Pages 317–334 (1956), published by Maruzen K. K., it exhibits a circular-dichroic Cotton effect ($[\theta]_{225\,nm} = -48,000$).

(8) Solubility: It is soluble in methanol, ethanol, acetone, diethyl ether, ethyl acetate, n-hexane, chloroform, carbon tetrachloride, methylene chloride and benzene. It is insoluble in water.

(9) $R_f$ value: It gives $R_f$ value of 0.53 in thin layer chromatography on silica gel 60 $PF_{254}$ (thickness of layer: 0.5 mm, developing solvent: ethyl acetate-n-hexane (1:9), distance of development: 16 cm, temperature of development: room temperature).

(10) Gas chromatography: It elutes at a retention time of 5.8 minutes in gas chromatography (fixed phase: Gaschrome Q (which is a flux-calcined diatomite support manufactured by Jhons Manvilles Celite Co.) containing 3% Silicone OV-1 (which is composed mainly of methylphenyl silicone manufactured by Ohio Valley Co., U.S.A.), 100–120 meshes, column dimension: 3 mm in diameter and 1 m in length, carrier gas: nitrogen, flow rate: 50.3 ml/min., pressure: 0.6 kg/cm², column temperature: 130° C., detector: hydrogen flame ionization detector).

The novel compound SF-2 has the following chemical reactivities:

(1) When sprayed with 0.5% vanillin-sulfuric acid on a thin layer of silica gel 60 $PF_{254}$ and then heated, it first assumes red-violet and afterwards turns to blue-violet.

(2) When reduced with lithium aluminum hydride ($LiAlH_4$) in ether, it forms an alcohol ($C_{15}H_{24}O$).

(3) When oxidized in acetone by Jone's reagent (cf. L. F. Fieser and M. Fieser: "Reagents for Organic Syntheses", John Wiley and Sons, Corp., 1967, Vol. 1, Page 142), it forms a carboxylic acid ($C_{15}H_{22}O_2$). The latter reacts with diazomethane to give a methyl ester ($C_{16}H_{24}O_2$).

From the physicochemical properties and chemical reactivities mentioned above, it can be deduced that SF-2 substance is 5-isopropyl-8-methyl bicyclo[5.3.0-]deca-2,8-diene-2-carboaldehyde having the following structural formula:

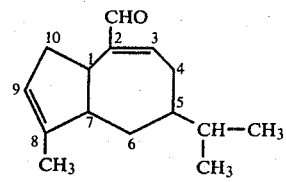

Next, SF-1 and SF-2 substances, mentioned above, can be produced by cultivating a microbial strain belonging to Genus Sclerotinia and having an ability to produce these compounds, and collecting SF-1 and SF-2 substances from the cultivated mixture. Any microorganisms may be used so far as they have an ability to produce SF-1 substance and SF-2 substance, among which Sclerotinia S-1 is particularly preferable.

Sclerotinia S-1 is a new microbial strain which has been isolated by the present inventors from plums infested with Monilia disease and rotten in an orchard in Nagano Prefecture. It is deposited in Fermentation Research Institute, Agency of Industrial Science and Technology, Japan, as FERM-P No. 4214 and in American Type Culture Collection as ATCC No. 20497.

Sclerotinia S-1 has the following microbiological properties:

I. Growing state in culture media (cultivated in darkness for 7 days at pH 5.3 at 25° C.)

1. Malt extract agar medium

Color of colony: The surface is generally light brown colored without formation of pigment.

Shape of colony: It is smooth and flat as a whole and has ripples in concordance with growth. Adhesion of spore is flourishing at the height of waves. No wrinkles are observed on the front and back sides.

Growth: The growth of colony is rather good (diameter 35–45 mm) and extension of hyphase is poor.

Spore: All the spores formed are egg-shaped arthrospores having diameters of 6–7.5μ×12–15μ. FIG. 8 illustrates the reproduced view of microscopic photograph (×450) of Sclerotinia S-1 cultivated in darkness at 25° C. for 7 days in a malt extract agar medium (pH 5.3). It demonstrates that the hyphae have constructed ends to form arthrospores.

2. Czapek's agar medium

Color of colony: It is white-colored without formation of pigment.

Shape of colony: The central part is white-colored but it has a feeling of extended cotton due to the poor growth.

Growth: Very bad (diameter 5–10 mm).

Spore: Only a small number of arthrospores are observed due to the poor growth.

3. Sabouraud's agar medium

Color of colony: It is generally light brown colored with excellent extension of hyphase. The central part is white-colored. No pigment is formed.

Shape of colony: The span of microbial growth is uneven. No wrinkles are observed on the front and back sides. As a whole, it has a feeling of cotton dust.

Growth: Good (diameter 25–45 mm).

Spore: All the spores formed are arthrospores. They are egg-shaped and have diameters of 6–7.5μ×12–15μ.

II. Physiological and morphological properties
 1. Growing temperature: 10°–45° C.
 2. Optimum temperature for the growth: 25°–26° C.
 3. Growing pH: 3.0–9.0
 4. Optimum pH for the growth: 5.0–6.0
 5. Other noteworthy character: It flourishingly forms arthrospores in darkness.

Based on the above-mentioned microbiological properties of Sclerotinia S-1, as well as on the observation of the microorganisms growing on rotten plum and the microscopic observation of them, the Sclerotinia S-1 herein considered was identified according to the classification method mentioned in E. A. Bessay: "Morphology and Taxonomy of Fungi" (1952) and Makoto Hiura: "Shokubutsu Byogenkinrui Kaisetsu" (1967). As the result, it was judged that this strain belongs to Family Sclerotiniaceae because the strain forms discal ascocarp on the tip of long manubrium growing from sclerotium and the ascocarp has no opercle and that the strain belongs to Genus Sclerotinia of Family Sclerotiniaceae because formation of carpospore is not observed. Additionally saying, Genus Monilinia belonging to Family Sclerotiniaceae is definitely distinguishable from Genus Sclerotinia because it forms carpospore of the type of imperfect fungi Genus Monilinia though it resembles Genus Sclerotinia. Accordingly, the strain herein considered is doubtlessly judged to be a new microbial strain belonging to Genus Sclerotinia.

SF-1 and SF-2 substances of this invention can be produced synthetically. In order to produce them by a fermentative process, however, one cultivates Sclerotinia S-1 (FERM-P No. 4214, ATCC 20497) by the method of solid culture or preferably by the method of liquid culture. As the medium, those containing nitrogen and carbon sources are used. As said nitrogen source, for example, meat extract, peptone, corn steep liquor, gluten, casein, yeast extract, urea, amino acid or the like is used either alone or in mixture of two or more members. As said carbon source, for example, sucrose, glucose, maltose, lactose, millet jelly, Koji extract, starch, bagasse, wheat bran, molasse, glycerol or the like is used either alone or in mixture of two or more members. Besides above, inorganic substances such as ammonium sulfate, potassium phosphate, magnesium chloride, sodium chloride iron, manganese, molybdenum or the like, and vitamins, oils and fats, etc. may also be added.

The culture is carried out usually at a temperature of 20° to 32° C., at a pH value of 6.0 to 7.0, for a period of 5 to 10 days.

It is needless to say that natural and artificial varieties of Sclerotinia S-1 can also be used in the same manner as above.

The SF-1 and SF-2 substances of this invention can be isolated from cultivated mixture and purified in the following manner. Thus, the cultivated mixture is extracted with an organic solvent by the usual method first of all. Examples of the solvent usable for the extraction include ethyl acetate, acetone, benzene, diethyl ether, chloroform and mixtures thereof. Subsequently, SF-1 substance is separated from SF-2 substance by an appropriate combination of various procedures such as fractional precipitation, distillation, adsorption, thin layer chromatography, column chromatography, counter current partition and the like, whereby SF-1 and SF-2 substances can be obtained in the purified forms. In the fractional precipitation, methanol, ethanol, acetone, dioxane or the like or mixtures thereof is used as organic solvent. In the chromatographies, silica gel, silicic acid, magnesium silicate, diatomaceous earth, active charcoal, alumina or the like, for example, is used as adsorbent.

By appropriately selecting sodium sulfite method by the use of carbonyl reagent, Girard reagent method, phenylhydrazine method, etc., it is also possible to separate SF-1 and SF-2 substances from each other and to obtain various derivatives thereof. When treated according to the conventional method described in, for example, Yuki Kagobutsu Kakuninho, Vol. 1, Pages 325–624 (1954), Yokendo, these derivatives give pure SF-1 and SF-2 substances.

Having an action of markedly stimulating the sporulation of various microorganisms, particularly of molds, the SF-1 and SF-2 substances of this invention are important from the viewpoint of industrial cultivation of molds. For example, the ability of molds to produce antibiotics such as cephalosporin or to produce enzymes such as protease and amylase will remarkably be improved by using the compounds of this invention.

Referring to the following examples, the production process of the SF-1 and SF-2 substances of this invention and their effect will be illustrated concretely, but the present invention is not limited thereto.

EXAMPLE 1

A mixture consisting of 4 liters of distilled water and 800 g of sliced potatoes was boiled for 1 hour, and the boiled mixture was filtered with a gauze. Eighty g of sugar and 80 g of agar were added to 4 liters of the filtrate, the mixture was sterilized in an autoclave at 120° C., and then it was divided into 20 ml portions and poured into 200 Petri dishes. After solidification, mycelia of Sclerotinia S-1 (FERM-P No. 4214, ATCC No. 20497) were uniformly inoculated thereonto under aseptic conditions and then subjected to stationary culture in darkness in an incubator at 30° C. for 7 days at a pH value of 6.5.

After completion of the culture, the cultivated mixture was crushed into pieces and macerated with 6 liters of acetone. The acetone extract was concentrated under reduced pressure to 1 liter of the aqueous residue. The concentrate was thoroughly extracted with 3 liters of ethyl acetate. The ethyl acetate extract thus obtained was subjected to preparative thin layer chromatography on silica gel (Kieselgel 60 PF$_{254}$, Merck Corp.) at 25° C. with n-hexane-ethyl acetate (3:7) as a developing solvent. The active fractions having R$_f$ value of 0.6–0.8 were collected and eluted with ethyl acetate to obtain crude SF-1 substance.

The crude SF-1 substance thus obtained was purified in the following manner. Thus, it was again subjected to similar preparative thin layer chromatography by changing the solvent composition into a 3:7. The active fractions obtained were recrystallized to remove the major part of ergosterol. Subsequently, the remainder was again subjected to thin layer chromatography in the same manner as above, the active fractions having R$_f$ value of 0.6–0.7 were collected, and they were eluted with ethyl acetate. The eluate was subjected to high performance liquid chromatography by the use of a column having a diameter of 4 mm and a length of 250 mm and packed with silica gel (LiChrosorb RP-2, manufactured by Merck Co.) with dioxane-water mixture (6:4) as a developing solvent. The active fractions eluting in 5 to 8 minutes were collected by detecting UV$_{234}$ nm absorption, whereby a pure sporogenic substance SF-1 was obtained.

The mass spectrum, proton nuclear magnetic resonance spectrum, infrared absorption spectrum, and ultraviolet absorption spectrum of the thus obtained SF-1 substance are illustrated in FIGS. 1, 2, 3, and 4, respectively.

Experimental Example 1

The SF-1 substance thus obtained has the aforementioned properties. The results of sporogenic activity test are mentioned below.

A potato-sucrose agar medium prepared in the same manner as in Example 1 was divided into 5 ml portions and poured into test tubes. The test tubes were stoppered with cotton and the contents were solidified to give slant media. The surfaces of the slant media were uniformly coated with each 30 μl of a solution of SF-1 substance obtained as above in ethyl acetate having varied concentration, after which one platinum loop quantity of Sclerotinia S-1 (the same as used in Example 1) was inoculated to the center of each slant medium, stoppered with cotton, and cultivated in an incubator at 30° C. for 4 days under the light of 7500 luxes emitted from a fluorescence lamp. The number of spores formed in a circular region, having a diameter of 5 mm, on the hyphae-growing surface was counted under microscope. As a control, the same medium as above was coated with 30 μl of ethyl acetate not containing SF-1 substance and then inoculated and cultivated in the same manner as above. In some of the control runs, the test tube was completely enveloped with aluminum foil to bring the content to darkness and the same test was performed. In this test, all the procedures were carried out aseptically. The results obtained are summarized in Table 1.

Table 1

| Concentration of SF-1 substance (ppm) | Illuminating condition | Spore number |
|---|---|---|
| 0 (Control) | Light | 70 |
| | Dark | 1218 |
| 0.0005 | Light | 110 |
| 0.001 | " | 181 |
| 0.01 | " | 257 |
| 0.1 | " | 367 |
| 1.0 | " | 533 |
| 5.0 | " | 962 |

The results clearly demonstrate that when the cultivation is carried out under illumination of light without addition of SF-1 substance of this invention, the sporulation progresses hardly, whereas when SF-1 substance is added, the sporulation is induced to a great extent even under illumination of light and the effect of SF-1 substance to include the sporulation increases with its quantity. The control experiment carried out in darkness demonstrates that Sclerotinia S-1 quite actively forms spore in darkness.

EXAMPLE 2

A mixture consisting of 8 liters of distilled water and 1600 g of potato was boiled for 1 hour, and the boiled mixture was filtered with a gauze. One hundred sixty g of sucrose and 160 g of agar were added to 8 liters of the filtrate, the mixture was sterilized in an autoclave at 120° C., and then it was divided into 20 ml portions and poured into 400 Petri dishes. After solidification, mycelia of Sclerotinia S-1 (FERM-P No. 4241, ATCC 20497) were uniformly inoculated thereto under aseptic conditions and subjected to stationary culture in darkness in an incubator at 30° C. for 7 days.

After completion of the culture, the cultivated mixture was crushed into pieces and extracted with 12 liters of acetone. The acetone extract was concentrated under reduced pressure to 3 liters of the aqueous residue. The concentrate was thoroughly extracted with 5 liters of ethyl acetate. The ethyl acetate layer was dried over anhydrous sodium sulfate and concentrated, after which the resulting ethyl acetate extract was subjected to preparative thin layer chromatography on silica gel (Kiesel gel 60 $PF_{254}$, Merck corp.) at 25° C. with n-hexane-ethyl acetate mixture (3:7) as a developing solvent. The active fractions having $R_f$ value of 0.8–1.0 were collected and eluted with ethyl acetate to obtain a crude product.

The crude product thus obtained was purified in the following manner. Thus, it was subjected to column chromatography on silicic acid by stepwise elution of each one liter of 100% n-hexane, 1%, 2%, 3%, 4% and 5% ethyl acetate in n-hexane as developing solvents. The 1% ethyl acetate-n-hexane fractions obtained were concentrated under reduced pressure. Then, the concentrate was subjected to preparative thin layer chromatography on silica gel 60 $PF_{254}$ (20×20 cm, thickness 0.5 mm) at 25° C. with ethyl acetate-n-hexane (1:9) as a developing solvent. The active fractions having $R_f$ value of 0.50 to 0.55 were collected and eluted with ethyl acetate. Subsequently, the active fractions were again subjected to preparative thin layer chromatography on silica gel by developing twise with 3% ethyl acetate-n-hexane as a developing solvent. The active fractions having $R_f$ value of 0.5 to 0.6 were collected and eluted with ethyl acetate. The solvent was removed under reduced pressure, and there was obtained a pure SF-2 substance. It had the aforementioned properties.

The mass spectrum, proton nuclear magnetic resonance spectrum, and ultraviolet absorption spectrum of the thus obtained SF-2 substance are illustrated in FIGS. 5, 6 and 7, respectively.

Experimental Example 2

The SF-2 substance thus obtained was subjected to sporogenic activity test. The results were as shown below.

A potato-sucrose agar medium prepared in the same manner as in Example 2 was divided into 5 ml portions and poured into test tubes, stoppered with cotton and solidified to give slant media. The surfaces of the slant media were coated with each 30 μl of a solution of SF-2 substance in ethyl acetate having varied concentration. One platinum loop quantity of Sclerotinia S-1 (the same as used in Example 2) was inoculated to the center of each slant medium, stoppered with cotton, and cultivated under the light of 7500 luxes emitted from a fluorescence lamp in an incubator at 30° C. for 3 days. The number of spores formed in a circular region having a diameter of 5 mm on the hyphae-growing surface was counted under microscope. As a control, the same medium as above was coated with 30 μl of ethyl acetate not containing SF-2 substance, after which it was inoculated and cultivated in the same manner as above. In some of the control runs, the test tube was completely enveloped with aluminum foil to bring the content to a darkness and the same test was performed. In this test, all the procedures were carried out aseptically. The results obtained are summarized in Table 2.

Table 2

| Concentration of SF-2 substance (ppm) | Illuminating condition | Spore number |
| --- | --- | --- |
| 0 (Control) | Light | 8 |
|  | Dark | 73 |
| 0.05 | Light | 15 |
| 0.1 | " | 15 |
| 0.5 | " | 21 |
| 1.0 | " | 28 |
| 2.0 | " | 46 |
| 5.0 | " | 62 |

The results clearly demonstrate that when the cultivation is carried out under illumination of light without addition of SF-2 substance of this invention, the sporulation progresses hardly, whereas when SF-2 substance is added the sporulation is induced to a great extent even under illumination of light and the effect of SF-2 to induce the sporulation increases with its quantity. The control experiment carried out in darkness demonstrates that Sclerotinia S-1 (FERM-P No. 4214, ATCC 20497) quite actively forms spore in darkness.

What is claimed is:

1. 5-Isopropyl-8-methyl bicyclo[5.3.0]deca-2,8-diene-2-carboxylic acid having a chemical structure represented by the formula

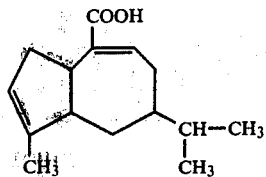

2. 5-Isopropyl-8-methyl bicyclo[5.3.0]deca-2,8-diene-2-carboxylic acid according to claim 1 which has a molecular formula of $C_{15}H_{22}O_2$, shows the following signals in mass spectrum:

m/e (relative intensity %): 234 (M+, 31), 191 (49), 189 (9), 173 (16), 147 (30), 145 (30), 135 (36), 123 (24), 117 (20), 105 (38), 91 (base peak 100), 77 (40), 69 (46), 57 (73), 43 (36), 41 (86), shows the following signals in proton nuclear magnetic resonance spectrum (measured in deuterated chloroform at 100 MHz):

δ: 0.84 (3H, d, J=7.1 Hz), 0.92 (3H, d, J=7.1 Hz), 1.69 (3H, s), 1.3—2.4 (10H, m), 2.60 (1H, broad d, J=12.5 Hz), 5.49 (1H, broad s), 7.13 (1H, t, J=3.7 Hz), shows a characteristic infrared absorption spectrum (cm$^{-1}$: 3425, 2960, 2940, 1690, 1655, 1550, 1460, 1410, 1385, 1270, 1250, 1040), and shows $R_f$ value of 0.50 in thin layer chromatography on silica gel [thickness of layer: 0.25 mm, developing solvent: ethyl acetate-n-hexane (3:7), developing distance: 16 cm].

* * * * *